United States Patent [19]

Harris et al.

[11] Patent Number: 5,138,020
[45] Date of Patent: Aug. 11, 1992

[54] PHOSPHATE SALTS OF MONOMERS FOR PBZ AND THEIR USE IN PREPARING PBZ POLYMERS

[75] Inventors: William J. Harris, Midland, Mich.; Ming-Biann Liu, Clayton, Calif.; Luke R. Kleiss, Evanston, Ill.; Zenon Lysenko; Steven Rosenberg, both of Midland, Mich.

[73] Assignee: The Dow Chemical Company, Midland, Mich.

[21] Appl. No.: 341,502

[22] Filed: Apr. 21, 1989

[51] Int. Cl.$^5$ .................. C08G 73/06; C08G 73/22; C08G 69/28

[52] U.S. Cl. .................. 528/185; 528/179; 528/183; 528/184; 528/207; 528/208; 528/210; 528/211; 528/286; 528/289; 528/290; 528/291; 528/336; 528/337; 528/339; 528/341; 528/377; 558/169; 568/8

[58] Field of Search ............ 558/169; 528/337, 185, 528/179, 183, 184, 207, 208, 210, 211, 339, 336, 341, 286, 289–291, 377; 568/8

[56] References Cited

U.S. PATENT DOCUMENTS

| | | | |
|---|---|---|---|
| 2,852,513 | 9/1958 | Schroder | 558/169 |
| 3,304,349 | 2/1967 | Shen | 558/169 |
| 4,148,624 | 4/1979 | Maier | 558/169 |
| 4,169,932 | 10/1979 | Sokolov et al. | 528/337 |
| 4,359,567 | 11/1982 | Evers | 528/179 |
| 4,533,692 | 8/1985 | Wolfe et al. | 528/183 |
| 4,533,693 | 8/1985 | Wolfe et al. | 528/185 |
| 4,533,724 | 8/1985 | Wolfe et al. | 528/313 |
| 4,578,432 | 3/1986 | Tsai et al. | 528/179 |
| 4,703,103 | 10/1987 | Wolfe et al. | 528/179 |
| 4,766,244 | 8/1988 | Lysenko | 564/418 |
| 4,772,678 | 9/1988 | Sybert et al. | 528/179 |
| 4,774,350 | 9/1988 | Wakatsuki et al. | 558/169 |

OTHER PUBLICATIONS

"Polybenzazoles," Makromol. Chem. 179 (1965).
Maximovich et al., "Fabrication and Evaluation of New Resins," Final Technical Report AFWAL-TR-8-0-4090 (Jul. 1980).
11 Ency. Poly. Sci. & Eng., *Polybenzothiazoles and Polybenzoxazoles*, 601 (J. Wiley & Sons, Inc.).

*Primary Examiner*—John Kight, III
*Assistant Examiner*—P. Hampton-Hightower

[57] ABSTRACT

PBZ polymers are synthesized by the reaction of AA- and BB-monomers. The BB-monomer is conveniently synthesized and isolated as a phosphate salt having a uniform number of phosphate ions associated with each BB-monomer ion. Such high purity monophosphate and diphosphate salts can be obtained by precipitating the monomer from an aqueous acid solution by adjusting the pH balance or from a mixture of phosphoric acid and a volatile, polar, saturated organic liquid at a relatively low temperature.

66 Claims, No Drawings

PHOSPHATE SALTS OF MONOMERS FOR PBZ AND THEIR USE IN PREPARING PBZ POLYMERS

STATEMENT OF GOVERNMENT INTEREST

This invention was made with Government support under contract number F33615-85-C-5113 awarded by the Department of the Air Force. The Government has certain rights in this invention.

BACKGROUND OF THE INVENTION

The invention relates to the synthesis of polybenzoxazole (PBO), polybenzimidazole (PBI) or polybenzothiazole (PBT) and related polymers (hereinafter referred to as PBZ polymers).

AA/BB-PBZ polymers are a known class of polymers which contain a plurality of mer units comprising:
(1) a first aromatic group ($Ar^1$),
(2) a first azole ring which is fused with the first aromatic group,
(3) a second azole ring which is fused with the first aromatic group, and
(4) a divalent organic group (DL), which is inert with respect to all reagents for making PBZ polymers under polymerization conditions, bonded by a single bond to the 2-carbon of the second azole ring.

Mer units are preferably linked by a single bond from the divalent organic group (DL) to the the the 2-carbon in the first azole group of an adjacent unit.

Mer units in AA/BB-PBZ polymers preferably comply with Formula 1

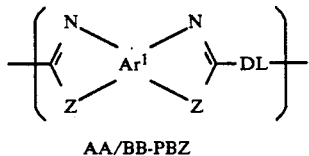

AA/BB-PBZ wherein:
$Ar^1$ is a first aromatic group as previously described:
DL is a divalent organic group as previously described: and
each Z is independently chosen from the group consisting of —O—, —S— or —NR—, wherein R is an aliphatic or aromatic group which does not interfere with polymerization.

PBZ polymers, their chemical structure, their properties and their synthesis are described in depth in a number of references such as 11 Ency. Poly. Sci. & Eng., *Polybenzothiazoles and Polybenzoxazoles.* 601 (J. Wiley & Sons 1988): Wolfe et al., *Liquid Crystalline Polymer Compositions and Process and Products.* U.S. Pat. No. 4,703,103 (Oct. 27, 1987): Tsai et al., *Method for Making Heterocyclic Block Copolymer,* U.S. Pat. No. 4,578,432 (Mar. 25, 1986); Wolfe et al., *Liquid Crystalline Poly(2,6-Benzothiazole) Compositions, Process and Products,* U.S. Pat. No. 4,533,724 (Aug. 6, 1985); Wolfe, *Liquid Crystalline Polymer Compositions, Process and Products.* U.S. Pat. No. 4,533,693 (Aug. 6, 1985) and Wolfe et al., *Liquid Crystalline Polymer Compositions and Process and Products,* U.S. Pat. No. 4,533,692 (Aug. 6, 1985), which are incorporated herein by reference.

AA/BB-PBZ polymers are synthesized by the reaction of a BB-monomer comprising:
(1) a first aromatic group ($Ar^1$):
(2) a first o-amino-basic moiety containing:
(a) a primary amine group bonded to the first aromatic group, and
(b) a hydroxy, thio or amine group bonded to the first aromatic group in ortho position with respect to the primary amine group: and
(3) a second o-amino-basic moiety bonded to the first aromatic group,
and an AA-monomer comprising:
(1) a divalent organic moiety (DL) which is inert with respect to all reagents under reaction conditions: and
(2) two "electron-deficient carbon groups," as that term is hereinafter defined, bonded to said divalent organic moiety (DL).

BB-monomers are extremely sensitive to air oxidation in their free amine state. For that reason, BB-monomers are typically isolated and stored as hydrogen chloride salts, which are more stable. See Chenevey et al., *Process for Preparing Shaped Articles of Rigid Rod Heterocyclic Liquid Crystalline Polymers,* U.S. Pat. No. 4,606,875 (Aug. 19, 1986) at Column 4, lines 29-49; and Choe, *Process for the Production of High Molecular Weight Para Ordered Aromatic Heterocyclic Polymer,* U.S. Pat. No. 4,423,202 (Dec. 27, 1983) at Column 3, lines 1-10.

The hydrogen halide salts of BB-monomers are difficult to polymerize, so that the hydrogen halide is removed from the monomer in a "dehydrohalogenation step" prior to polymerization. See, e.g., Choe, *Process for the Production of High Molecular Weight Para Ordered Aromatic Heterocyclic Polymer,* U.S. Pat. No. 4,423,202 (Dec. 27, 1983) at Column 4, lines 38-52. The dehydrohalogenation step causes the release of two moles of hydrogen halide gas, typically hydrogen chloride gas, for each mole of monomer reacted. The gas is corrosive and limits the materials from which equipment can be made. Furthermore, the gas causes substantial foaming in the thick solutions used for the synthesis of PBZ polymers. Foaming reduces the efficiency of mixing in the system, which must be vigorous to form high molecular weight polymer, and necessitates the use of reaction vessels having sufficient extra volume to accommodate the foam. Finally, the dehydrohalogenation step is time consuming and lowers the economic efficiency of the PBZ polymerization.

Prior art processes have relied upon elaborate staging processes to minimize the foaming within manageable limits. See Wolfe et al., *Liquid Crystalline Polymer Compositions and Process and Products,* U.S. Pat. No. 4,703,103 (Oct. 27, 1987) at column 53, line 55 to column 56, line 4; Wolfe, *Liquid Crystalline Polymer Compositions, Process and Products.* U.S. Pat. No. 4,533,693 (Aug. 6, 1985) at column 42, line 61 to column 44, line 66: and Wolfe et al., *Liquid Crystalline Polymer Compositions and Process and Products,* U.S. Pat. No. 4,533,692 (Aug. 6, 1985) at column 39, line 59 to column 42, line 11, which are incorporated herein by reference. Those processes do not eliminate foaming. They eliminate neither the need to use specific materials in the equipment nor the need to take the time for dehydrohalogenation.

What is needed is a process for forming a reactive solution of BB-monomer in mineral acid which does not require a dehydrohalogenation step.

SUMMARY OF THE INVENTION

One aspect of the present invention is a compound comprising:

(1) at least one BB-monomer ion; and
(2) at least one phosphate ion
having a substantially uniform ratio of phosphate ions associated with each BB-monomer ion.

A second aspect of the present invention is a compound comprising
(1) at least one BB-monomer ion; and
(2) at least one phosphate ion
said compound being in a crystalline form.

A third aspect of the present invention is a process for recovering the diphosphate salt of a BB-monomer, which process comprises precipitating said BB-monomer diphosphate salt from a solution containing phosphoric acid and a volatile, polar, saturated-organic liquid which is miscible with phosphoric acid.

A fourth aspect of the present invention is a process for recovering the monophosphate salt of a BB-monomer, which process comprises raising the pH of an aqueous solution containing phosphoric acid and BB-monomer ions such that a BB-monomer monophosphate salt precipitates.

A fifth aspect of the present invention is a process for forming a PBZ polymer comprising the steps of:
(a) preparing a solution containing a mineral acid and a BB-monomer phosphate salt of substantially known BB-monomer content; and
(b) contacting said BB-monomer in said mineral acid solution with an AA-monomer in an amount and under conditions such that a PBZ polymer is formed.

The third and fourth aspects of the present invention are processes which can be used to make BB-monomer phosphate salts, which are part of the first and second aspects of the present invention. Those BB-monomer phosphate salts can be used in the process of the present invention to make useful PBZ polymers having a high average molecular weight. PBZ polymers can be spun to make fibers or extruded to make films, and those fibers and films can be used in structural applications, such as reinforcement for composites, according to known methods such as those described in 11 Ency. Poly. Sci. & Eng., supra. at 625-32, which is incorporated herein by reference.

DETAILED DESCRIPTION OF THE INVENTION

Definitions

The following terms, which are used repeatedly throughout this application, have the meanings and preferred embodiments set out hereinafter unless otherwise specified.

Aromatic group (Ar)—any aromatic ring or ring system which can be part of a PBZ polymer. Each aromatic group may individually be heterocyclic, but each is preferably carbocyclic and more preferably hydrocarbyl. If an aromatic group is heterocyclic, it is preferably a nitrogen-containing heterocycle.

Each aromatic group may comprise a single aromatic ring, a fused ring system, or an unfused ring system, containing two aromatic moieties linked by a bond or a divalent linking moiety which is inert with respect to PBZ polymerization reagents under PBZ polymerization conditions. If the aromatic group comprises a divalent linking moiety, that moiety preferably comprises an ether linking moiety, a thioether linking moiety, a sulfonyl linking moiety, an alkyl linking moiety, or a halogenated alkyl linking moiety or known equivalents. The divalent linking moiety preferably comprises no more than about 6 carbon atoms. Aromatic groups preferably consist essentially of a single ring.

Size is not critical as long as the aromatic group is not so big that it prevents further reactions of the moiety in which it is incorporated. Each aromatic group preferably independently comprises no more than about 18 carbon atoms, more preferably no more the about 12 carbon atoms and most preferably no more than about 6 carbon atoms, excluding any divalent linking group and any organic substituent on the aromatic group.

Each aromatic group may independently have substituents which are stable in mineral acid and which do not interfere with the polymerization of monomers for PBZ synthesis, such as halogen atoms, alkoxy moieties, aryloxy moieties or alkyl moieties. Substituents which comprise organic moieties preferably comprise no more than about 12 carbon atoms, more preferably no more than about 6 carbon atoms. Each aromatic group preferably has no substituents other than those specified hereinafter.

Azole ring—an oxazole, thiazole or imidazole ring. The carbon atom bonded to both the nitrogen atom and the oxygen, sulfur or second nitrogen atom is the 2-carbon, as depicted in formula 2

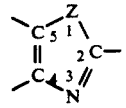

wherein Z is —O—, —S— or —NR—; and R is hydrogen, an aromatic group, an aliphatic group or an aliphatic-aromatic group, preferably hydrogen or an alkyl group, and most preferably hydrogen. R preferably comprises no more than about 6 carbon atoms, more preferably no more than about 4 and most preferably no more than about 1. Each azole ring is independently preferably oxazole or thiazole and more preferably oxazole. In PBZ polymers, the 4 and 5 carbon atoms are ordinarily fused with an aromatic group.

Azole-forming moiety—an "o-amino-basic moiety" "electron-deficient carbon group," as those terms are hereinafter defined.

o-Amino-basic moiety—a moiety bonded to an aromatic group, which o-amino-basic moiety contains
(1) a first primary amine group bonded to the aromatic group and
(2) a hydroxy, thiol or primary or secondary amine group bonded to the aromatic group ortho to said primary amine group.

It preferably comprises a hydroxy, thiol or primary amine moiety, more preferably comprises a hydroxy or thiol moiety, and most preferably comprises a hydroxy moiety If the o-amino-basic moiety comprises two amine groups, preferably both are primary amine groups. If the o-amino-basic moiety contains a secondary amine group, the secondary amine group may comprise an aromatic or an aliphatic group but preferably comprises an alkyl group. The secondary amine group preferably comprises no more than about 6 carbon atoms, more preferably no more than about 4 carbon atoms and most preferably no more than about 1 carbon atom.

Electron-deficient carbon group (Q)—any group containing a carbon atom which can react in the mineral acid with an o-amino-basic moiety to form an azole ring, such as the groups listed in column 24, lines 59-66 of the 4,533,693 patent, which is incorporated herein by reference, and such as an orthoester group, an imidate ester group, a trihalomethyl group or an alkali metal carboxylate group. Each electron-deficient carbon group is preferably independently a carboxylic acid or acid halide group and more preferably a carboxylic acid group. Halogens in electron-deficient carbon groups are preferably independently chlorine, bromine or fluorine and are more preferably chlorine.

Mineral acid—a non-oxidizing liquid acid capable of dissolving PBZ polymers, such as sulfuric acid, methanesulfonic acid, polyphosphoric acid and mixtures thereof. The mineral acid highly preferably either is a dehydrating acid or contains a dehydrating agent such as $P_2O_5$ Examples of preferred mineral acids include polyphosphoric acid and mixtures of methanesulfonic acid and phosphorus pentoxide. Polyphosphoric acid preferably has a $P_2O_5$ content by weight of at least about 70 percent, more preferably at least about 75 percent and preferably has a $P_2O_5$ content of at most about 90 percent, more preferably at most about 85 percent. The ratio of methanesulfonic acid to phosphorus pentoxide in mixtures of those compounds is preferably no more than about 20:1 by weight and no less than about 5:1 by weight. The most preferred mineral acid is polyphosphoric acid.

PBZ polymer—A polymer from the group of polybenzoxazoles and polybenzobisoxazoles (PBO), polybenzothiazoles and polybenzobisthiazoles (PBT) and polybenzimidazoles or polybenzobisimidazoles (PBI). For the purposes of this application, the term "polybenzoxazole (PBO)" refers broadly to polymers in which each unit contains an oxazole ring bonded to an aromatic group, which need not necessarily be a benzene ring. The term "polybenzoxazole (PBO)" also refers broadly to poly(phenylene-benzo-bis-oxazole)s and other polymers wherein each unit comprises a plurality of oxazole rings fused to an aromatic group. The same understandings shall apply to the terms polybenzothiazole (PBT) and polybenzimidazole (PBI). As used in this application, the term also encompasses mixtures, copolymers and block copolymers of two or more PBZ polymers, such as mixtures of PBO, PBT and/or PBI and block or random copolymers of PBO, PBI and PBT.

Rigid Rod PBZ polymer—An "intrinsic" or "articulated" rigid rod PBZ polymer as the terms "intrinsic" and "articulated" are defined in Hwang, "Processing, Structure and Properties of Liquid Crystalline PBT Polymer", Kansai Committee of the Society of Fiber Science and Technology, Japan, Post Symposium on Formation, Structure and Properties of High Modulus and High Tenacity Fibers 23–26 (Aug. 26, 1985); Evers et al, "Articulated All-Para Polymers with 2,6-Benzobisoxazole, 2,6-Benzobisthiazole, and 2,6-Benzobisimidazole Units in the Backbone," 14 Macromolecules 925 (1981): Evers, "Thermooxidatively Stable Articulated Benzobisoxazole and Benzobisthiazole Polymers," 24 J. Poly. Sci. Part A 1863 (1986) and Evers et al., *Articulated Para-Ordered Aromatic Heterocyclic Polymers Containing Diphenoxybenzene Structures*, U.S. Pat. No. 4,229,566 (Oct. 21, 1980).

Intrinsic rigid rod polymers are essentially rectilinear and have a persistence length comparable to their contour length. Articulated rigid rod polymers comprise a plurality of essentially rectilinear moieties joined by a relatively small number of non-linear moieties. Rigid rod PBZ polymers used in the present invention are preferably intrinsic rigid rod polymers. If articulated, they preferably comprise on average no more than about one non-linear mer unit for each 9 essentially rectilinear mer units.

Monomer and Synthesis

In the present invention an AA/BB-PBZ polymer is synthesized using a phosphate salt of a BB-monomer. The polymerization of PBZ is a condensation polymerization. It is ordinarily vital to employ a 1:1 stoichiometry of AA- and BB-monomers in a condensation polymerization if high average molecular weight is desired. However, the BB-monomer is dibasic and phosphoric acid contains three acidic hydrogen atoms. A given sample of BB-monomer phosphate salt may therefore contain any mixture of BB-monomer monophosphate salt, BB-monomer diphosphate salt, salts in which three phosphate ions are associated with two BB-monomer ions, and so forth. In a mixed sample it is difficult to ascertain precisely what weight of the sample results from BB-monomer ion and what weight results from phosphate counterion. However, the correct stoichiometry cannot be reached unless the BB-monomer content and purity of the sample is known. Therefore, the BB-monomer phosphate sample must be composed primarily of salts in which the ratios of BB-monomer ions and phosphate ions are substantially consistent and identifiable. Compounds of the present invention meet that criterion.

Compounds of the present invention comprise ions of a BB-monomer, said BB-monomer having the description previously set out in the Background of the Invention. o-Amino-basic moieties in the BB-monomer preferably comprise a hydroxy group or a thio group and more preferably comprise a hydroxy group.

If the BB-monomer is to produce rigid rod PBZ, then the first aromatic group should be a single ring or a fused ring system. Furthermore, the o-amino-basic moieties should be bonded to the first aromatic group in a position such that each moiety in the first o-amino-basic moiety is para to a moiety in the second o-amino-basic moiety, i.e., the first o-amino-basic moiety is in 1 and 2 position and the second o-amino-basic moiety is in 4 and 5 position on a single ring; or the first o-amino-basic moiety is in 2 and 3 position and the second o-amino-basic moiety is in 6 and 7 position on a system of two fused rings; and so on. In all other respects, the first aromatic group should conform to the description and preferred embodiments previously set out. The first aromatic group is most preferably a 1,2,4,5-phenylene moiety.

If a non-rigid-rod thermoplastic PBZ polymer is desired, then the first aromatic group is preferably an unfused ring system comprising two aromatic moieties linked by a divalent linking group or a bond, as previously described. The o-amino-basic moieties are preferably bonded to separate aromatic moieties. The divalent linking group more preferably comprises an ether linking group or a sulfonyl linking group. In all other respects, the first aromatic group should conform to the description and preferred embodiments previously set out. Examples of suitable first aromatic groups include the 3,4,3',4'-diphenylene ether moiety, the 3,4,3',4'-biphenylene moiety and the 3,4,3',4'-diphenylene sulfone moiety.

The BB-monomer ion is preferably an ion of 4,6-diaminoresorcinol, 2,5-diaminohydroquinone, 2,5- diamino-1,4-dithiobenzene, or 1,2,4,5-tetraaminobenzene.

BB-monomer can be synthesized by known processes, such as those described in Lysenko, U.S. Pat. No. 4,776,244 (Aug. 23, 1988): in Inbasekaren et al., U.S. Pat. No. 4,806,688 (Feb. 21, 1989): and in U.S. Pat. No. 4,533,693 Tables 1, 2 and 3, columns 19-24 and the references described therein, which are incorporated herein by reference. For instance, BB-monomers may be synthesized by nitrating a halogenated diol or related compound and reducing the nitro groups to form primary amines.

The free-base BB-monomer synthesized by the processes described above is converted to a phosphate salt in solution by contacting with a source of phosphate ion, such as phosphoric acid. The contact may be during or immediately after synthesis of the BB-monomer. For instance, when a dinitro intermediate is reduced to form the BB-monomer, that reduction may be carried out in the presence of phosphoric acid, so that the free-base BB-monomer is protonated essentially as it is formed. Alternatively, the free-base BB-monomer may be formed under non-oxidizing conditions and then contacted with phosphoric acid prior to contact with air or any other oxidizing medium. Either process should be carried out under a non-oxidizing atmosphere. The temperature is not critical for salt formation. It may be room temperature or any other temperature convenient for synthesis of the BB-monomer.

Alternatively, the BB-monomer hydrogen halide salt may be formed according to known processes, and then converted at a later time to the BB-monomer phosphate. The hydrogen halide salt may be converted to the phosphate salt by contact with phosphoric acid under known dehydrohalogenation conditions. Elevated temperatures are preferable. The displacement of hydrogen halide by phosphoric acid is preferably carried out at no less than about the freezing point of the solution, more preferably at no less than about 15° C., and most preferably no less than about 40° C. The temperature for the displacement should be out at which the BB-monomer is stable. It is preferably no more than about 70° C., more preferably no more than about 65° C. and most preferably no more than about 55° C. Alternatively, hydrogen chloride can be removed from the BB-monomer by titrating the hydrogen chloride salt with base under non-oxidizing conditions. Thereafter, phosphoric acid may be added.

The BB-monomer is preferably contacted with at least a stoichiometric amount of phosphoric acid, based upon the phosphate salt which is desired. More preferably, the solution contains an excess of phosphoric acid at least sufficient to keep the pH of the solution low enough to prevent precipitation of any BB-monomer monophosphate salt. For instance, the excess of phosphoric acid is preferably at least about 10 mole percent over the stoichiometric amount and more preferably at least about 20 mole percent. The maximum quantity of phosphoric acid is not critical and is limited primarily by practical considerations, when the diphosphate salt is to be recovered. It is preferably no more than about 10 moles of phosphoric acid per mole of BB-monomer. When the monophosphate salt is desired, then the excess of phosphoric acid is preferably low enough to minimize the concentration of inorganic phosphate salts in the resulting BB-monomer phosphate salt. Preferably, no more than about 2.5 moles of phosphoric acid per mole of BB-monomer are used: more preferably no more than about 2.0 moles: and most preferably no more than about 1.5 moles.

Contacting the BB-monomer with phosphoric acid yields a solution containing BB-monomer ions and phosphate ions. The desired BB-monomer phosphate salt is recovered from the solution by precipitation under appropriate conditions.

The BB-monomer diphosphate salt is recovered by precipitating from a mixture of phosphoric acid and a volatile, polar, saturated-organic liquid. Preferably, either the phosphoric acid or the volatile, polar, saturated-organic liquid is added directly to the solution in which the BB-monomer or diphosphate salt was synthesized. For instance, the dinitro intermediate of the BB-monomer may be reduced in a solution of volatile, polar, saturated-organic liquid, and phosphoric acid may be added to the resulting solution: or BB-monomer hydrochloride salt may be converted to the phosphate salt in a phosphoric acid solution and volatile, polar, saturated-organic liquid may be added to the resulting solution. Alternatively, the BB-monomer diphosphate can be recrystallized from a fresh solution of phosphoric acid and volatile, polar, saturated-organic liquid.

The volatile, polar, saturated-organic liquid preferably comprises no more than about 6 carbon atoms, more preferably no more than about 4 carbon atoms and most preferably no more than about 3 carbon atoms. It preferably comprises at least about 2 carbon atoms and more preferably at least about 3 carbons. It preferably forms an azeotropic mixture with water. It is more preferably an alcohol and most preferably n-propanol. It is theorized that when the volatile, polar, saturated-organic liquid forms an azeotrope with water and solvates phosphoric acid, it removes water and phosphoric acid from the BB-monomer diphosphate as that precipitated salt is dried. It is further theorized that the absence of water and unreacted phosphoric acid in the crystal may extend the shelf-life of the resulting BB-monomer phosphate salt.

The solution from which the BB-monomer diphosphate is precipitated should contain sufficient volatile, polar, saturated-organic liquid and phosphoric acid to precipitate primarily the diphosphate salt. The solution preferably comprises by weight at least about 9 percent phosphoric acid, and more preferably at least about 20 percent. The solution preferably comprises by weight at least about 50 percent volatile, polar, saturated-organic liquid, and more preferably at least about 75 percent.

Precipitation may be accomplished either by adding the volatile, polar, saturated-organic liquid or phosphoric acid to a solution at a temperature low enough for precipitation to occur, or by forming the solution at a higher temperature and cooling the solution to a temperature at which precipitation occurs. The temperature at which the BB-monomer diphosphate salt precipitates from the solution depends, in a manner familiar to persons skilled in the art, upon the BB-monomer ion; the volatile, polar, saturated-organic compound: the ratio of volatile, polar, saturated-organic compound to phosphoric acid: the strength of the phosphoric acid: and other factors. The temperature should be below the boiling point and above the freezing point of the solution from which precipitation will occur. It can be readily determined without undue experimentation. To precipitate diphosphate salts of 4,6-diaminoresorcinol or 1,4-diamino-2,5-dithiobenzene from a preferred solution of phosphoric acid and n-propanol, the solution temperature is preferably at most about 25° C., more preferably at most about 5° C., and most preferably at most about 0° C.

The precipitated BB-monomer diphosphate is preferably washed with cold volatile, polar, saturated-organic compound to remove residual phosphoric acid. It is preferably dried under high temperature or low pressure or both.

BB-monomer monophosphate salt precipitates from aqueous phosphoric acid solutions by adjusting the pH of the solution to a level at which the monophosphate is insoluble. The solution should contain sufficient water to prevent coprecipitation of any inorganic salts which are formed in raising the pH. The precise pH level necessary for precipitation varies depending upon the BB-monomer, the temperature of the solution, the concentration of phosphoric acid in the solution, and other factors. Preferred pH for precipitation for individual monomers and conditions can readily be determined without undue experimentation by persons of ordinary skill in the art. When the BB-monomer is 4,6-diaminoresorcinol, the pH achieved to cause precipitation is preferably at least about 2, more preferably at least about 3.8, and most preferably at least about 4.0. The pH of the system should remain low enough that the BB-monomer remains stable with respect to air oxidation. The pH achieved to cause precipitation is preferably below 7, more preferably at most about 5.5, and most preferably at most about 4.1.

Preferably, the monophosphate salt is precipitated from a solution of relatively lower pH by adding a base to neutralize part of the acid and raise the pH of the solution. Examples of suitable bases include alkali metal and ammonium hydroxides, phosphates, hydrophosphates, bicarbonates and carbonates. The base preferably comprises a carbonate or bicarbonate anion, and more preferably comprises a bicarbonate anion. The base preferably comprises an ammonium or sodium cation, and more preferably a sodium cation. The most preferred base is sodium bicarbonate.

Inorganic phosphates formed during the neutralization of phosphoric acid can sometimes coprecipitate with the BB-monomer salt and contaminate the product. For instance the reaction with sodium hydroxide produces sodium dihydrogen phosphate, disodium hydrogen phosphate and trisodium phosphate. Contamination by insoluble inorganic phosphate salts is preferably limited by one or more techniques.

First, the total concentration of partially neutralized phosphoric acid in the system can be kept low by limiting the excess quantity of phosphoric acid used. Preferred maxima for the quantity of phosphoric acid are previously set out.

Second, insoluble inorganic phosphates are more likely to be formed in areas of the solution having a relatively high base concentration. Therefore, the base is preferably added with vigorous mixing sufficient to make the concentration of base essentially uniform throughout the entire solution.

Third, precipitated inorganic phosphates can be leached out of the precipitate by agitating in an aqueous medium in which the BB-monomer salt is insoluble. The precipitate is preferably maintained in the precipitating solution at moderate elevated temperatures with vigorous mixing for a period of time after the precipitation is completed. The maximum temperature is preferably less than 60° C. and more preferably no more than about 55° C. and most preferably no more than about 40° C. The minimum temperature is governed primarily by practical considerations. The reaction proceeds faster at higher temperatures than at lower temperatures. The temperature is preferably at least about 15° C. and more preferably at least about 30° C. At about 30° C. to about 40° C. and pH of about 4, the precipitate is preferably agitated in solution for at least 30 minutes to 1 hour.

The precipitated monophosphate monomer is preferably washed with an aqueous acid solution and then dried. Until drying is complete, the damp monomer is preferably handled under a vacuum or an inert atmosphere such as nitrogen. Complete drying is preferred because retained water in the BB-monomer phosphate may cause error in stoichiometric calculations and may reduce the oxidative stability of the salt. Drying may be accomplished by known techniques, such as centrifuging or press-filtering followed by distillation of any remaining water under vacuum. The temperature of the distillation is preferably less than 60° C., more preferably no more than 55° C. and most preferably no more than about 40° C. It is preferably at least about 0° C. and more preferably at least about 30° C.

In BB-monomer phosphate salts of the present invention, the ratio of BB-monomer ions to phosphate ions is sufficiently uniform and reproducible to permit substantially accurate calculation of the stoichiometry of a PBZ polymerization. Preferably, the ratio of phosphate ions associated with each BB-monomer ion is uniform for at least about 90 percent of the BB-monomer ions. More preferably, the ratio of phosphate ions associated with each BB-monomer ion is uniform for at least about 95 percent of the BB-monomer ions. Most preferably, the ratio of phosphate ions associated with each BB-monomer ion is uniform for at least about 99 percent of the BB-monomer ions. Adequate purity of the BB-monomer phosphate salt can alternatively be demonstrated by the fact that the monomer is crystalline. Diphosphate salts precipitated under the preferred conditions of the present invention are preferably crystalline.

The BB-monomer salt is highly preferably 4,6-diaminoresorcinol diphosphate, 3,6-diaminohydroquinone diphosphate, 4,6-diaminoresorcinol monophosphate, 3,6-diaminohydroquinone monophosphate or 1.4-diamino-2,5-dithiobenzene diphosphate having the purity previously described.

Polymerization Process

In the polymerization process of the present invention, a BB-monomer having a substantially known BB-monomer content is contacted with an AA-monomer in mineral acid in an amount and under conditions such that a PBZ polymer is formed. By "substantially known BB-monomer content," it is meant that the BB-monomer content of the sample is known with sufficient definiteness to permit reaction of the AA- and BB-monomers in a stoichiometry sufficient to produce consistently high molecular weight polymer. The actual BB-monomer content of the sample is preferably known within 10 weight percent of the calculated content, more preferably within 5 weight percent, more highly preferably within 2 weight percent, and most preferably within 1 weight percent. Compounds of the present invention are particularly useful because the appropriate molar content of BB-monomer can often be calculated based upon the weight of the sample. The BB-monomer content of the sample can also be analyzed by known means, such as chromatography analysis, elemental analysis or NMR, and the reaction stoichiometry can be adjusted accordingly.

The AA-monomer has the description and preferred embodiments previously set out in the Background of the Invention. Electron-deficient carbon groups in the AA-monomer have the description and preferred embodiments previously set out, and are most preferably carboxylic acid moieties.

The divalent organic moiety (DL) of the AA-monomer preferably comprises an alkyl group, a halogenated alkyl group or an aromatic group ($Ar^2$). The divalent organic moiety more preferably comprises an aromatic group ($Ar^2$) If a rigid rod polymer is desired, divalent organic moiety (DL) is preferably a single aromatic ring or two unfused aromatic moieties linked by a bond, and the electron-deficient carbon groups are preferably bonded to the aromatic group in para position with respect to each other or, for the two unfused rings, with respect to the other aromatic ring. For instance, examples of suitable AA-monomers for rigid rod PBZ include terephthalic acid, 4,4'-bis(benzoic acid), 2,5-pyridinedicarboxylic acid, and acid halides thereof. If a non-rigid-rod PBZ polymer is desired, then the divalent organic moiety (DL) preferably comprises a halogenated alkyl moiety, an alkyl moiety, an aromatic moiety with the electron-deficient carbon groups in meta position, or an unfused aromatic group containing two aromatic moieties linked by a divalent linking moiety. Examples of suitable AA-monomers for non-rigid-rod PBZ include isophthalic acid, oxy-bis(benzoic acid), sebacic acid and the acid halides thereof.

Examples of suitable AA-monomers and sources 4,533,693 at column 24, line 50 to column 32, line 49, which is incorporated herein by reference. Phosphate monomer will polymerize with halogen-containing AA-monomers, such as terephthaloyl chloride. However, the use of halogenated AA-monomers introduces halogen into the system and, therefore, defeats a significant advantage of the BB-monomer phosphate over the BB-monomer hydrogen halide salt. Preferably, electron-deficient carbon groups on the AA-monomer do not contain any halogen. The AA-monomer is preferably micronized before it is added to the mineral acid, particularly if it is highly insoluble in the reaction mixture, such as terephthalic acid or 4,4'-bis(benzoic acid).

Obvious variations of known polymerizations may be practiced using BB-monomer phosphates. The reaction may be practiced using mixtures of at least two different AA-monomers and/or BB-monomers to form random copolymers, as described in U.S. Pat. No. 4,703,103 in columns 57–74, which is incorporated herein by reference. Some AB-monomer may be added to the system to form random copolymers containing both AB- and AA/BB-monomer units. Terminating monomers (monofunctional reactants) comprising only a single o-amino-basic group or only a single electron-deficient carbon group can be added to the reaction mixture, as described in U.S. Pat. No. 4,703,103 in columns 41–47, which is incorporated herein by reference. If said terminating monomers comprise an o-amino-basic group, they are preferably produced as a phosphate salt or a free amine.

The polymerization takes place in mineral acid having the description and preferred embodiments previously described. The mineral acid is most preferably polyphosphoric acid. It is theorized that the phosphate ions in the monomer salt are quickly incorporated into the polyphosphoric acid solvent when the monomer is added to polyphosphoric acid. The monomer does not evolve hydrogen chloride, so no dehydrohalogenation step is necessary. The reaction can be commenced in polyphosphoric acid having a relatively high $P_2O_5$ content, such as between about 82 percent and about 86 percent. However, the BB-monomer phosphate is sometimes a very light fluffy crystal which is difficult to dissolve completely in very viscous polyphosphoric acid solutions. Therefore, it may be desirable to mix the monomer in a less viscous polyphosphoric acid solution having a $P_2O_5$ content of 76 percent or less, and then add more $P_2O_5$ to the solution to increase the $P_2O_5$ content to at least about 82 percent.

The reaction is preferably carried out under an inert atmosphere, such as nitrogen, helium or argon. When neither the AA-monomer nor the BB-monomer evolve halogen during the reaction, no dehydrohalogenation step is necessary. However, it is still preferable to react the reagents initially at a relatively low temperature to form low molecular weight oligomers, before raising the temperature to complete the reaction. The temperature of the preliminary reaction should be low enough that monomers do not become unstable. It is preferably no more than about 70° C., more preferably no more than about 65° C. and most preferably no more than about 55° C. It should be high enough that oligomers can form at a reasonably fast rate. It is preferably at least about 40° C. and more preferably at least about 45° C. After the preliminary reaction, the temperature is preferably raised in a stepwise fashion. The temperature of the reaction preferably reaches at least about 90° C., more preferably at least about 150° C. and most preferably at least about 190° C. The temperature of the reaction should stay below that at which the solvent and products substantially degrade. Preferably, the reaction temperature is less than 250° C., more preferably no more than about 220° C. and most preferably no more than about 210° C.

Techniques which are useful for enhancing the molecular weight of PBZ polymer made by prior art processes are also useful to enhance the molecular weight of PBZ polymer made using BB-monomer phosphate salts. As already mentioned, it is useful to micronize AA-monomer which is insoluble in the reaction mixture, and it is useful to prereact the monomers at a relatively lower temperature to form low molecular weight oligomers before increasing the temperature to one suitable for complete reaction.

If the BB-monomer phosphate salt contains some unhydrolyzed oxidized impurities, it can be contacted with a reducing agent immediately before or during polymerization. A reducing agent which is stable in mineral acid and does not interfere with the polymerization may be added directly to the polymerization solution before polymerization. The reducing agent is preferably tin (II) dichloride or one of its hydrates. The reducing agent is added to the solution in an amount sufficient to convert substantially all of the oxidized impurity to monomer. Preferably, the BB-monomer sample comprises by mole no more than about 10 percent oxidized impurity, more preferably no more than about 5 percent, more highly preferably no more than about 2 percent and most preferably essentially none. The molar ratio of reducing agent to BB-monomer is preferably at least 2 percent, and more preferably at least 3 percent. It is preferably no more than about 10 percent, more preferably no more than about 5 percent and most preferably no more than about 3 percent.

If the BB-monomer is thought to contain slight impurities, such as non-uniform salts or oxidized impurities, a slight excess of AA-monomer over the calculated stoichiometric amount may be added. It has been reported that relatively large excesses of AA-monomer in the polymerization solution do not substantially lower the molecular weight of the resulting polymer. See Tsai et al., "High Strength/High Modulus Aromatic Heterocyclic ABA Block Copolymers," Final Report AFWAL-TR-87-4072 (published May, 1987), which is incorporated herein by reference. Molar excesses of AA-monomer up to 10 percent or higher may be tolerated, although it is preferable that the molar excess of AA-monomer be no more than about 5 percent. On the other hand, molar excesses of BB-monomer cause substantial reductions in the molecular weight of the resulting PBZ polymer.

If the actual BB-monomer content of the phosphate salt is the same as or slightly less than the calculated content, polymerization in the presence of an excess of AA-monomer should not substantially reduce the molecular weight of the polymer. If the actual BB-monomer content of the phosphate salt is higher than the calculated content, then the additional AA-monomer should prevent that variation from upsetting the stoichiometry of the reaction. The excess of AA-monomer may be any amount which is sufficient to make up for variations in the BB-monomer content of the phosphate salt without substantially reducing the molecular weight of the resulting polymer. The excess is preferably no more than about 10 percent over the calculated stoichiometric amount, more preferably no more than about 5 percent, and most preferably no less than about 1 percent.

The polymers formed by the process of the present invention are similar to those described in the Background of the Invention and the references incorporated therein. They preferably have a weight average molecular weight of at least 15,000; more preferably at least 20,000: and most preferably at least about 25,000. Inherent viscosities will, of course, vary substantially from polymer to polymer. However, rigid rod PBO or PBT preferably has an inherent viscosity in methanesulfonic acid at about 25° C. and a concentration of 0.05 g/dL of at least about 10 dL/g, more preferably at least about 15 dL/g, more highly preferably at least about 20 dL/g and most preferably at least about 25 dL/g.

The polymers may be extruded into films, or spun into fibers for use in fiber matrix composites, by means familiar to persons of ordinary skill in the art, such as are described in 11 Ency. Poly. Sci. & Eng., supra, at 625-32: Chenevey et al., *Process for Preparing Shaped Articles of Rigid Rod Heterocyclic Liquid Crystalline Polymers*, U.S. Pat. No. 4,606,875 (Aug. 19, 1986); Chenevey et al., *Process for Preparing Film of Poly{[Benzo(1,2-D:4,5-D')bisthiazole-2.6-diyl]-1,4-phenylene, its Cis Isomer or Mixtures Thereof*, U.S. Pat. No. 4,487,735 (Dec. 11, 1984): Tan, *Process for Producing High-Strength, Ultralow Denier Polybenzimidazole* (PBI) *Filaments*, U.S. Pat. No. 4,263,245 (Apr. 21, 1981): Hwang et al., "Solution Processing and Properties of Molecular Composite Fibers and Films," 23 Poly. Eng. & Sci. 784, 785 (1984): and Hwang et al., "Composites on a Molecular Level: Phase Relationships, Processing, and Properties," B22(2) J. Macromol. Sci.-Phys. 231, 234-35 (1983), which are incorporated by reference.

WORKING EXAMPLES

The examples contained herein are for illustrative purposes only and are not to be taken as limiting the scope of either the specification or the claims. Unless otherwise specified, all parts and percentages are by weight.

example 1

Synthesis of 4,6-diaminoresorcinol monophosphate salt

A solution of 5.00 g (0.0213 moles) of 2-chloro-4,6-dinitroresorcinol, 60 g of water, 4.92 g of 86 percent phosphoric acid (0.0432 moles), and 1.20 g of wet palladium-on-carbon catalyst containing 57.17 percent water is heated with stirring to 50° C. under 1 atmosphere pressure hydrogen atmosphere. The temperature and hydrogen pressure are maintained for 2 hours, at which time GC analysis of the solution indicates that the reaction is completed. The catalyst is recovered by filtering at 50° C. At 15° C., the pH of the solution is raised to 3.7 by adding a 10 percent aqueous sodium hydroxide solution. The title product precipitates and is recovered by filtration.

EXAMPLE 2

Synthesis of 4,6-diaminoresorcinol monophosphate salt

A mixture of 50 g (0.2347 moles) of 4,6-diaminoresorcinol di(hydrochloride) salt, 26.74 g of 86 percent phosphoric acid (0.2347 moles) and 796.3 g of water is agitated until a clear solution is formed. The temperature is increased to 40° C. A solution of 200 g (0.4694 moles) of diammonium hydrophosphate dissolved in 200 g of water is added dropwise over a period of 8 minutes, and a white slurry forms. The slurry is heated with agitation at 54° C. for one hour and then is cooled to 27° C. The title compound is filtered, washed with 200 g of water and dried under nitrogen atmosphere at room temperature. The recovered product weighs 52.67 g (91 percent yield). The product contains by weight 57 percent 4,6-diaminoresorcinol, 13.1 percent phosphorus and 0.28 percent chloride. The theoretical composition of the pure title compound should be 59 percent 4,6-diaminoresorcinol, 13.0 percent phosphorus and no chloride. This suggests that the recovered product is substantially all the title product.

EXAMPLE 3

Synthesis of 4,6-diaminoresorcinol monophosphate salt

A mixture of 260.7 g (1.111 moles) of 4,6-dinitro-2-chlororesorcinol, 270.2 g (2.370 moles) of 86 percent phosphoric acid, 15.66 g of 10 percent palladium-on-carbon and 1240 g of water is agitated under nitrogen atmosphere. Hydrogen is bubbled through the mixture at 50° C. for 6 hours, at which point a clear homogenous solution containing the catalyst is obtained. The catalyst is filtered and 10 g of stannous chloride dihydrate is added dissolved in 10 ml of 37 percent hydrochloric acid. Sodium bicarbonate is added to the stirred filtrate at 23° C. until a pH of 4 is achieved. The resulting slurry is filtered under nitrogen to obtain white crystals. The crystals are washed with an aqueous phosphoric acid solution having a pH of about 2.8. The crystals are then dried at room temperature by exposing to a flow of nitrogen gas.

The recovered crystalline product is about 254.39 g (88 percent yield). The crystals are analyzed using HPLC, Fourier-transform IR spectrometry, X-ray fluorescence, inductive coupled plasma spectroscopy and a Karl-Fischer Water analyzer. The analysis shows that the crystals contain about 95 percent pure of the title product. The product contains by weight about 54 percent BB-monomer, about 14+/−1.4 percent phosphorus, about 0.35+/−0.04 percent sodium, about 0.25+/−0.03 percent chloride and about 2.34 percent water.

EXAMPLE 4

Synthesis of 4,6-diaminoresorcinol monophosphate salt

The experiment of Example 2a is repeated, except that only 139.31 g (1.222 moles) of phosphoric acid is used. The crystalline product is additionally dried in a vacuum oven at 30° C. to 40° C. The recovered crystals are about 219.51 g (77 percent yield) of 99.7 percent pure product containing by weight about 55 percent BB-monomer, about 12.6+/−1.3 percent phosphorus, about 0.20+/−0.02 percent sodium and about 0.26 +/− 0.03 percent chloride.

EXAMPLE 5

Preparation of 4,6-diaminoresorcinol diphosphate salt from the corresponding dihydrochloride salt 4,6-Diaminoresorcinol dihydrochloride (200 g) is mixed with 500 ml of 85 percent phosphoric acid, 175 ml of water and 15 g of $Sn_2Cl_2 2H_2O$ predissolved in 50 ml of concentrated hydrogen chloride. The mixture is heated until a homogeneous solution is obtained. The solution is treated with 20 g of activated carbon and stirred with heating for 10 minutes. The solution is filtered while hot and 1.2 liters of n-propanol is added. The product begins to precipitate and the solution is cooled to 0° C. to complete the precipitation. The resulting white crystalline solid is isolated by filtration, washed with cold n-propanol, purged under a stream of dry nitrogen and vacuum dried at 30° C. overnight to a constant weight. Cis-PBO diphosphate monomer (268 g, 85 percent yield) is recovered. Elemental analysis indicates that the product contains 17.9 percent phosphorus.

EXAMPLE 6

Synthesis of the diphosphate salt of 4,6-diaminoresorcinol from 2-chloro-4,6-dinitroresorcinol 2-Chloro-4,6-dinitroresorcinol (50 g, 0.21 mole) and 16 g of ammonium acetate are added to 450 ml of n-propanol and 50 ml of water. The mixture is charged with 5.0 g of 10 percent palladium-on-carbon catalyst. The reactor is sealed, purged with nitrogen and charged to 100 psig with hydrogen gas. The hydrogen pressure is allowed to vary from 50 to 100 psig and the temperature of the reactor is maintained at 45° C. When hydrogen uptake is completed, the reactor is cooled to room temperature and purged with nitrogen. The reaction mixture is removed and treated with 200 ml of 85 percent phosphoric acid. The crude precipitate is isolated by filtration, washed with n-propanol and dried. It weighs 68 g. It is dissolved in 200 ml of 85 percent phosphoric acid containing 5 g of $Sn_2Cl_2 2H_2O$ predissolved in 20 ml of concentrated hydrogen chloride and 50 ml of water. The catalyst is removed by filtration and the solution is treated with 10 g of activated carbon. The solution is heated for 10 minutes, filtered and diluted with 650 ml of n-propanol. The solution is cooled to 0° C. and the product is isolated by filtration, washed with n-propanol and dried under a stream of nitrogen. The process yields 58 g of 4,6-diaminoresorcinol diphosphate salt.

EXAMPLE 7

Synthesis of 4,6-diaminoresorcinol diphosphate salt from 4,6-dinitroresorcinol 4,6-Dinitroresorcinol (75 g, 0.37 mole) and 5 g of 10 percent palladium-on-carbon catalyst are added to 1.5 liters of n-propanol. Hydrogen gas is charged into the reaction mixture while the temperature is maintained at 55° C. When uptake of hydrogen gas is completed, the reaction mixture is cooled to room temperature and 300 ml of 85 percent phosphoric acid is added. The resulting precipitate is isolated by filtration and recrystallized as described in Example 3. 4,6-Diaminoresorcinol diphosphate salt (97 g, 78 percent yield) is recovered.

EXAMPLE 8

Synthesis of 1,4-diamino-2,5-dithiobenzene diphosphate 1,4-Diamino-2,5-dithiobenzene dihydrochloride (20 g, 0.082 mole) is added to 150 ml of 85 percent phosphoric acid under nitrogen atmosphere. The mixture is heated until it becomes homogeneous. n-Propanol is added until a cloud point is observed and the reaction mixture is cooled to 0° C. The precipitate is isolated by filtration, washed with n-propanol to remove residual phosphoric acid and dried under a stream of anhydrous nitrogen gas. 1,4-Diamino-2,5-dithiobenzene diphosphate salt (29.1 g, 96 percent yield) is isolated.

EXAMPLE 9

Polymerization of 4,6-diaminoresorcinol monophosphate with terephthalic acid.

Under nitrogen atmosphere, 10 g of 4,6-diaminoresorcinol monophosphate from Example 3 (containing 0.038 mole diaminoresorcinol by LC analysis), 6.31 g (0.038 mole) of micronized terephthalic acid, and 17.4 g of phosphorus pentoxide are mixed with agitation in 29.5 g of 83.6 percent polyphosphoric acid. Nitrogen atmosphere and agitation are continued throughout the reaction. The mixture is heated at 90° C. for 8 hours, 150° C. for 8 hours and 190° C. for 24 hours. The resulting PBZ polymer is coagulated, washed thoroughly with water and dried. It has an inherent viscosity of about 18 dL/g as measured in methanesulfonic acid at 25° C. and a concentration of 0.05 g/dL.

EXAMPLE 10

Polymerization of 4,6-diaminoresorcinol monophosphate with terephthalic acid.

Under nitrogen atmosphere, 160 g of 4,6-diaminoresorcinol monophosphate (containing 0.661 mole diaminoresorcinol by LC analysis), 109.8 g (0.661 mole) of micronized terephthalic acid, 3.0 g (0.0133 mole) of tin (II) dichloride dihydrate, and 282 g of phosphorus pentoxide are mixed with agitation in 562 g of 83.6 percent polyphosphoric acid. Nitrogen atmosphere and agitation are continued throughout the reaction. The mixture is heated at 100° C.-110° C. for 3¼ hours, at 130° C. for 1 hour, at 145° C.-150° C. for 2 hours and at 210° C. for 2 hours. The resulting PBZ polymer is coagulated, washed thoroughly with water and dried. It has an inherent viscosity of about 22 dL/g as measured in methanesulfonic acid at 25° C. and a concentration of 0.05 g/dL. It is spun into a fiber by the process described in 11 Ency. Poly. Sci & Eng., supra at 625–32.

The fiber has a tensile strength of $4.55 \times 10^5$ psi and a tensile modulus of $4.12 \times 10^7$ psi.

EXAMPLE 11

Polymerization of 4,6-diaminoresorcinol diphosphate with terephthaloyl chloride

Under nitrogen atmosphere with stirring, 10.00 g of 4,6-diaminoresorcinol diphosphate, 6.34 g of terephthaloyl chloride and 22.9 g of polyphosphoric acid containing about 77 weight percent $P_2O_5$ are warmed at 45° C. for 16 hours. The mixture is warmed to 95° C. and two 10.7-g samples of $P_2O_5$ are added over a space of 8 hours with only slight foaming observed. The mixture is held at 150° C. for 16 hours and then at 190° C. for 24 hours. The title polymer is coagulated and washed in water, dried, ground, rewashed and redried. The polymer has an inherent viscosity of 24.1 dL/g in methanesulfonic acid at 25° C. and a concentration of 0.0508 g/dL.

EXAMPLE 12

Polymerization of 4,6-diaminoresorcinol diphosphate with terephthalic acid

Under nitrogen atmosphere with stirring, 10.00 g of 4,6-diaminoresorcinol diphosphate, 5.19 g of terephthalic acid and 21.5 g of polyphosphoric acid containing about 77 weight percent $P_2O_5$ are stirred for 5 minutes at room temperature. The mixture is warmed to 100° C. and two 10.8-g samples of $P_2O_5$ are added. The mixture is held at 100° C. for 10 minutes and then is warmed to 220° C. over a period of 15 minutes. The mixture is held at 220° C. for about 60 minutes. The title polymer is coagulated and washed in water, dried, ground, rewashed and redried. It has an inherent viscosity of 11.0 dL/g in methanesulfonic acid at 25° C. and a concentration of 0.0492 g/dL.

EXAMPLE 13

Polymerization of 4,6-diaminoresorcinol diphosphate with terephthalic acid

The procedure of Example 12 is followed except that after the $P_2O_5$ is added, the mixture is held at 100° C. for 2 hours, at 150° C. for 5 hours and at 190° C. for 16 hours. The resulting polymer is recovered as previously described and has an inherent viscosity of 16.2 dL/g in methanesulfonic acid at 25° C. and 0.0494 g/dL concentration.

EXAMPLE 14

Polymerization of 4,6-diaminoresorcinol diphosphate with terephthalic acid

The procedure of Example 13 is followed except that the initial charge of polyphosphoric acid is 18.2 g and the two samples of phosphorus pentoxide added each contain 12.5 g of phosphorus pentoxide. The resulting polymer has an inherent viscosity of 19.2 dL/g in methanesulfonic acid at 25° C. and 0.0474 g/dL concentration.

EXAMPLE 15

Polymerization of 1,4-diamino-2,5-dithiobenzene diphosphate with terephthalic acid Under nitrogen atmosphere, 10.00 g (27.2 mmoles) of 1,4-diamino-2,5-dithiobenzene diphosphate from Example 8, 4.74 g (28.5 mmoles) of terephthalic acid, 31.9 g of polyphosphoric acid containing 85 weight percent $P_2O_5$ and 13.8 g of $P_2O_5$ are mechanically stirred. The reaction mixture is heated for 2 hours at 100° C., for 5 hours at 150° C. and for 16 hours at 190° C. The title polymer is coagulated with water and extracted with water overnight in a soxhlet extractor. The product is ground, re-extracted and dried under vacuum overnight at 190° C. The polymer has an inherent viscosity of 26.9 dL/g in methanesulfonic acid at 25° C. and a concentration of 0.054 g/dL.

What is claimed is:

1. A solid BB-monomer monophosphate salt, comprising about a 1:1 molar ratio of:
   (1) ions of a BB-monomer that contains:
      (a) a first aromatic group;
      (b) a first o-amino-basic moiety containing: (i) a primary amine group bonded to the first aromatic group, and (ii) a hydroxy, thio or amine group bonded to the first aromatic group in ortho position with respect to the primary amine group; and
      (c) a second o-amino-basic moiety bonded to the first aromatic group;
   (2) phosphate ions.

wherein the average weight of BB-monomer in the salt is within about 10 percent of the calculated weight for a BB-monomer monophosphate salt.

2. The salt of claim 1 wherein the first aromatic group of the BB-monomer ion comprises no more than about 12 carbon atoms.

3. The salt of claim 2 wherein the first aromatic group of the BB-monomer ion is a carbocyclic group.

4. The salt of claim 3 wherein each o-amino-basic moiety of the BB-monomer ion independently comprises a hydroxy group or a thio group.

5. The salt of claim 4 wherein the first aromatic group of the BB-monomer is a single six-membered ring having no substituents other than those previously identified.

6. The salt of claim 1 wherein the BB-monomer ion is an ion of 1,2,4,5-tetraaminobenzene.

7. The salt of claim 1 wherein the BB-monomer ion is an ion of 4,6-diaminoresorcinol; 2,5-diaminohydroquinone or 2,5-diamino-1,4-dithiobenzene.

8. The salt of claim 7 wherein the average weight of BB-monomer in the salt is within about 5 percent of the calculated weight for a BB-monomer monophosphate salt.

9. The salt of claim 8 wherein the BB-monomer ion is an ion of 4,6-diaminoresorcinol.

10. The salt of claim 8 wherein the BB-monomer ion is an ion of 2,5-diaminohydroquinone.

11. The salt of claim 8 wherein the BB-monomer ion is an ion of 2,5-diamino-1,4-dithiobenzene.

12. A solid BB-monomer diphosphate salt, comprising about a 1:2 molar ratio of:
   (1) ions of a BB-monomer that contains:
      (a) a first aromatic group;
      (b) a first o-amino-basic moiety containing: (i) a primary amine group bonded to the first aromatic group, and (ii) a hydroxy, thio or amine group bonded to the first aromatic group in ortho position with respect to the primary amine group; and
      (c) a second o-amino-basic moiety bonded to the first aromatic group; and
   (2) phosphate ions.

wherein the average weight of BB-monomer in the salt is within about 10 percent of the calculated weight for a BB-monomer diphosphate salt.

13. The salt of claim 12 wherein the first aromatic group of the BB-monomer ion comprises no more than about 12 carbon atoms.

14. The salt of claim 13 wherein the first aromatic group of the BB-monomer ion is a carbocyclic group.

15. The salt of claim 14 wherein each o-amino-basic moiety of the BB-monomer ion independently comprises a hydroxy group or a thio group.

16. The salt of claim 15 wherein the first aromatic group of the BB-monomer is a single six-membered ring having no substituents other than those previously identified.

17. The salt of claim 12 wherein the BB-monomer ion is an ion of 1,2,4,5-tetraaminobenzene.

18. The salt of claim 12 wherein the BB-monomer ion is an ion of 4,6-diaminoresorcinol; 2,5-diaminohydroquinone or 2,5-diamino-1,4-dithiobenzene.

19. The salt of claim 18 wherein the average weight of BB-monomer in the salt is within about 5 percent of the calculated weight for a BB-monomer monophosphate salt.

20. The slat of claim 19 wherein the BB-monomer ion is an ion of 4,6-diaminoresorcinol.

21. The salt of claim 19 wherein the BB-monomer ion is an ion of 2,5-diaminohydroquinone.

22. The salt of claim 19 wherein the BB-monomer ion is an ion of 2,5-diamino-1,4-dithiobenzene.

23. A solid BB-PBO monomer salt, comprising:
1) ions of a BB-PBO monomer that contains:
   (a) a first aromatic group;
   (b) a first o-amino-hydroxy moiety containing: (i) a primary amine group bonded to the first aromatic group, and (ii) a hydroxy group bonded to the first aromatic group in ortho position with respect to the primary amine group; and
   (c) a second o-amino-hydroxy moiety bonded to the first aromatic group; and
(2) phosphate ions.

24. The salt of claim 23 wherein the first aromatic group comprises no more than about 18 carbon atoms.

25. The salt of claim 24 wherein aromatic rings in the first aromatic group are carbocyclic.

26. The salt of claim 25 wherein the first aromatic group contains no more than about 12 carbon atoms.

27. The salt of claim 23 wherein the first aromatic group is a substituted or unsubstituted tetravalent phenylene moiety.

28. The salt of claim 23 wherein the BB-PBO monomer ion is an ion of 4,6-diaminoresorcinol.

29. The salt of claim 23 wherein the BB-PBO monomer ion is an ion of 2,5-diaminohydroquinone.

30. The salt of claim 23 wherein the first aromatic group is a 3,4,3',4'-diphenylene ether moiety, a 3,4,3',4'-biphenylene moiety or a 3,4,3',4'-diphenyl sulfone moiety.

31. The salt of claim 23 wherein contains approximately two moles of phosphate ions for each mole of BB-PBO monomer ions.

32. The salt of claim 23 which contains approximately one mole of phosphate ions for each mole of BB-PBO monomer ions.

33. A process for recovering the diphosphate salt of a BB-monomer, which process compriess precipitating said BB-monomer diphosphate salt from a solution containing phosphoric acid and a volatile, polar, saturated-organic liquid which is miscible with phosphoric acid.

34. A process for recovering the monophosphate salt of a BB-monomer, which process comprises the steps:
(1) forming an aqueous solution containing a phosphoric acid and the BB-monomer; and
(2) contacting the solution of step (1) with a base in sufficient quantities to raise the pH of the solution to at least about 2, such that a BB-monomer monophosphate salt precipitates.

35. A process for forming a PBZ polymer comprising the steps of:
(a) mixing a selected amount of a BB-monomer phosphate salt with a mineral acid to form a solution having about a selected BB-monomer content: and
(b) contacting said BB-monomer in said mineral acid solution with about a stoichiometric amount of an AA-monomer under conditions such that a PBZ polymer is formed.

36. The process of claim 33 wherein the volatile, polar, saturated-organic liquid contains no more than about 6 carbon atoms per molecule and forms an azeotrope with water.

37. The process of claim 36 wherein the volatile, polar, saturated-organic liquid is an alcohol.

38. The process of claim 37 wherein the BB-monomer diphosphate salt is precipitated from a solution containing at least about 9 weight percent phosphoric acid and at least about 50 weight percent volatile, polar, saturated-organic liquid.

39. The process of claim 38 wherein the BB-monomer phosphate salt is precipitated at a temperature of no more than about 25° C.

40. The process of claim 39 wherein the BB-monomer is 4,6-diaminoresorcinol; 2,5-diaminohydroquinone or 2,5-dithio-1,4-diaminobenzene.

41. The process of claim 39 wherein the BB-monomer diphosphate salt is precipitated at temperatures down to at most about 5° C. from a solution containing at least about 75 weight percent of an alcohol having no more than about 4 carbon atoms and at least about 20 weight percent phosphoric acid.

42. The process of claim 34 wherein the pH of the solution is raised to less than 7.

43. The process of claim 34 wherein the pH of the solution is raised to at least about 3.8 and at most about 5.5

44. The process of claim 43 wherein the BB-monomer is 4,6-diaminoresorcinol; 2,5-diaminohydroquinone or 2,5-dithio-1,4-diaminobenzene.

45. The process of claim 44 wherein the pH is raised by adding a base containing alkali metal or ammonium ions and hydroxide, phosphate, hydrophosphate, bicarbonate or carbonate ions.

46. The process of claim 44 wherein the pH s raised by adding a base containing a carbonate or bicarbonate anion.

47. The process of claim 44 further comprising the step mixing the precipitated BB-monomer phosphate salt in an aqueous medium in which the slat is insoluble at a temperature between about 15° C. and about 60° C. for a period of time sufficient to leach out inorganic phosphates in the precipitated salt.

48. The process of claim 44 wherein the pH of the solution is raised to at most about 4.1.

49. The process of claim 35 wherein step (2) is carried out with agitation in a non-oxidizing and dehydrating mineral acid at a temperature which reaches at least about 150° C.

50. The process of claim 49 wherein the process proceeds from step (1) to step (2) without an intervening dehydrohalogenation step.

51. The process of claim 50 wherein the BB-monomer contains:
   (1) a first aromatic group;
   (2) a first o-amino-basic moiety containing:
      (a) a primary amine group bonded to the first aromatic group; and
      (b) a hydroxy or thio group bonded to the first aromatic group in an ortho position with respect to the primary amine group; and
   (3) a second o-amino-basic moiety, that has the same description as the first o-amino-basic moiety, bonded to the first aromatic group.

52. The process of claim 51 wherein the amount of AA-monomer in step (2) at least about equimolar and no more about a 10 percent molar excess.

53. The process of claim 51 wherein the AA-monomer is terephthalic acid; 4,4'-bis-(benzoic acid); 2,5-pyridenedicarboxylic acid; isophthalic acid; oxy-bis-(benzoic acid) or an alkyl dicarboxylic acid.

54. The process of claim 51 wherein the mineral acid is a polyphosphoric acid and/or a mixture of methanesulfonic acid and $P_2O_5$.

55. The process of claim 51 wherein step (2) occurs at a temperature between 40° C. and 250° C.

56. The process of claim 55 wherein step (2) is commenced at a temperature lower than the final temperature, and the temperature is increased during step (2) to a temperature of at least about 190° C.

57. The process of claim 51 wherein the BB-monomer is 4,6-diaminoresorcinol or 2,5-diaminohydroquinone or an analog thereof.

58. The process of claim 51 wherein the BB-monomer salt in step (1) is essentially a monophosphate salt.

59. The process of claim 51 wherein the BB-monomer salt in step (1) is essentially a diphosphate salt.

60. The process of claim 50 wherein the BB-monomer is 4,6-diaminoresorcinol; 2,5-diaminohydroquinone; or 2,5diamino-1,4-dithiobenzene.

61. The process of claim 60 wherein the the AA-monomer is terephthalic acid; 4,4'-bis-(benzoic acid); 2,5-pyridenedicarboxylic acid; isophthalic acid; oxy-bis-(benzoic acid) or an alkyl dicarboxylic acid.

62. The process of claim 61 wherein the mineral acid is polyphosphoric acid.

63. The process of claim 62 wherein step (2) is commenced at a relatively low temperature, and the temperature is increased during step (2) to a temperature of at least about 190° C.

64. The process o claim 63 wherein the $P_2O_5$ content of the polyphosphoric acid is lower at the commencement of the first step (1) than it is at the commencement of step (2).

65. The process of claim 63 wherein the salt is essentially a diphosphate salt.

66. The process of claim 63 wherein the salt is essentially a monophosphate salt.

* * * * *

UNITED STATES PATENT AND TRADEMARK OFFICE
CERTIFICATE OF CORRECTION

PATENT NO. : 5,138,020
DATED : August 11, 1992
INVENTOR(S) : William J. Harris; Luke R. Kleiss; Zenon Lysenko and Steven Rosenberg It is certified that error appears in the above-indentified patent and that said Letters Patent is hereby corrected as shown below:

On title page, "OTHER PUBLICATIONS" 3rd reference, after (J. Wiley & Sons, Inc.), insert -- 1988 --.

Column 18, line 22, after group;, insert -- and --.
Column 19, line 25, delete " slat " and insert -- salt --.
Column 19, line 58, delete " -diphenyl " and insert -- -diphenylene --.
Column 19, line 60, delete " wherein " and insert -- which --.
Column 20, line 15, delete " content: " and insert -- content; --.
Column 20, line 55, delete " s " and insert -- is --.
Column 20, line 60, delete " slat " and insert -- salt --.
Column 22, line 12, delete " 2,5diamino- " and insert
-- 2,5-diamino- --.
Column 22, line 23, delete " o " and insert -- of --.
Column 22, line 23, delete " P2O5content " and insert
-- P2O5 content --.

Signed and Sealed this

Sixteenth Day of November, 1993

Attest:

BRUCE LEHMAN

Attesting Officer

Commissioner of Patents and Trademarks